United States Patent

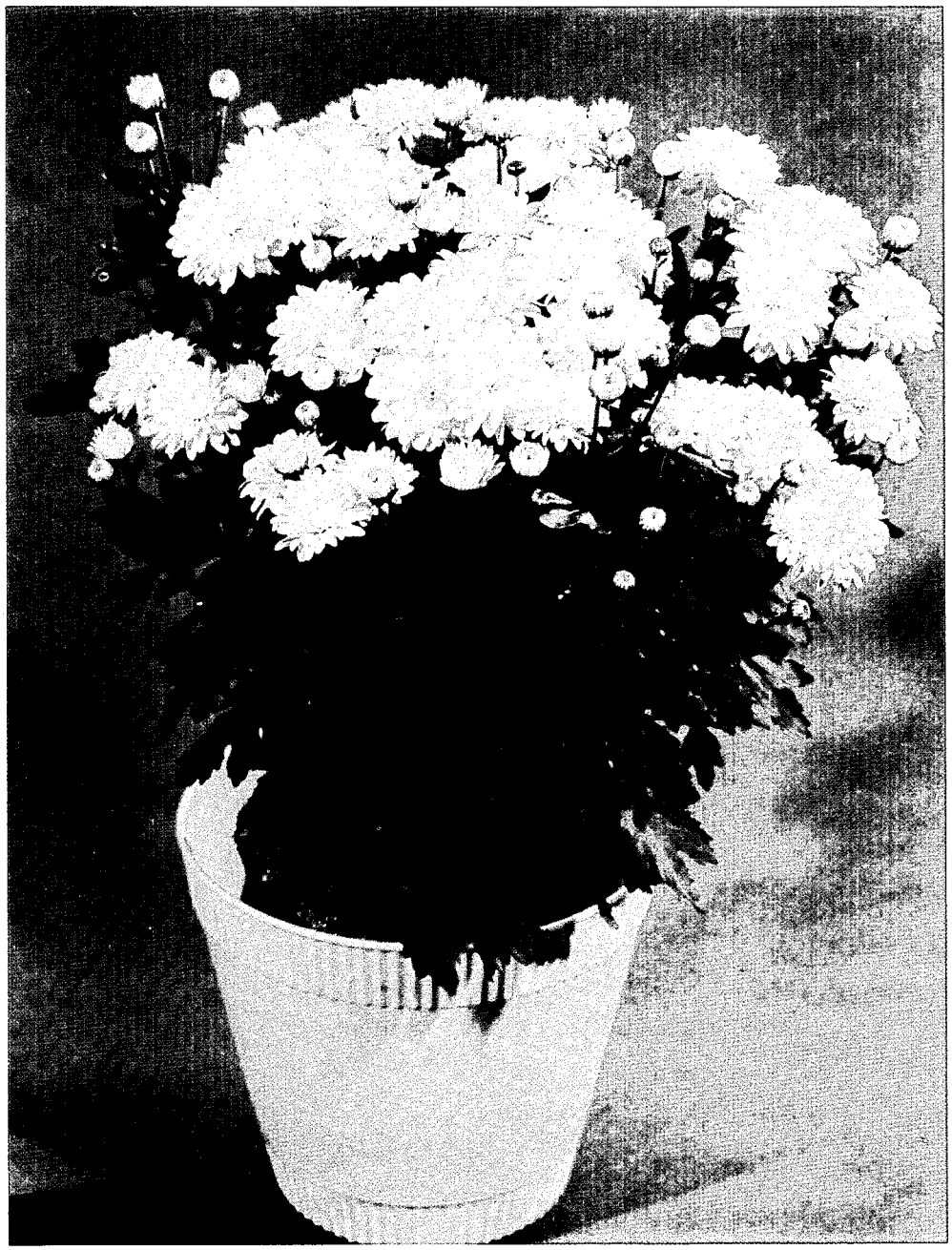

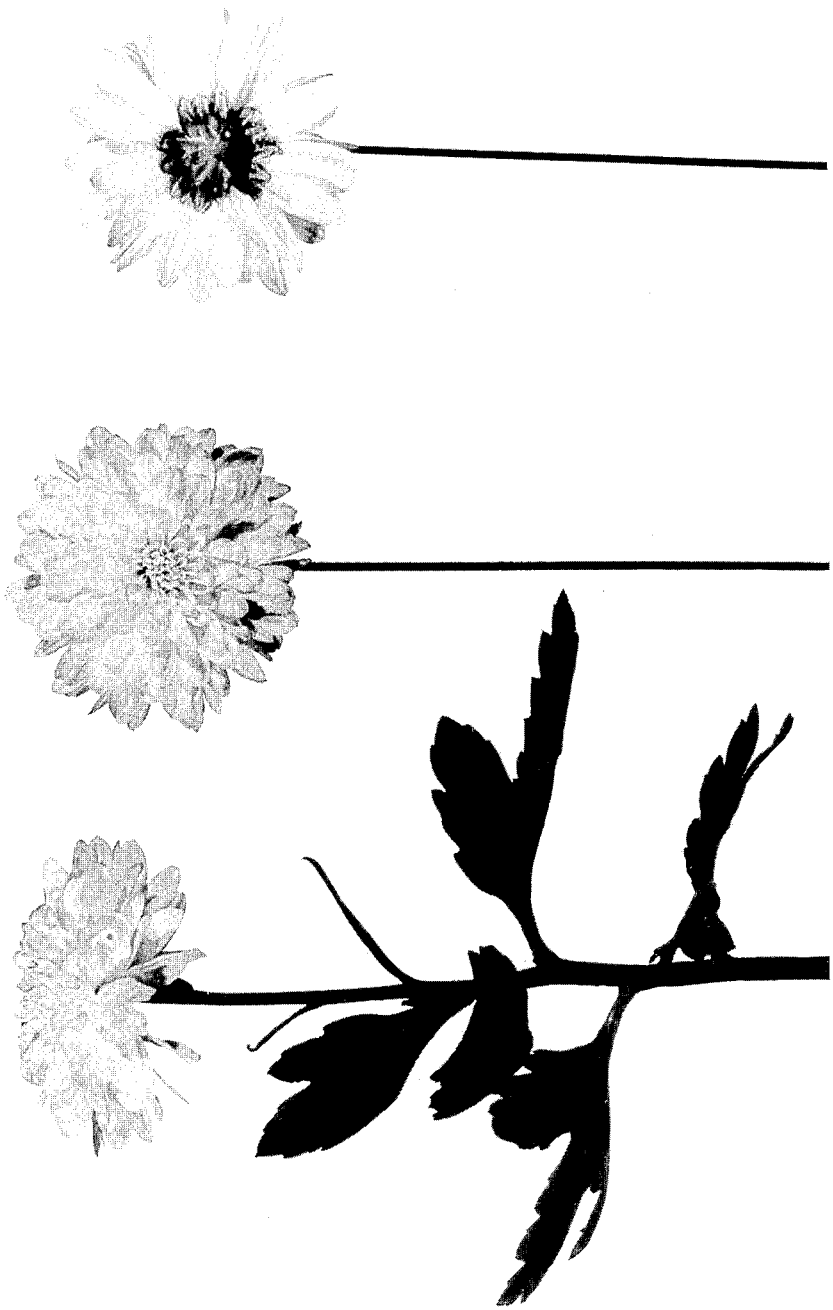

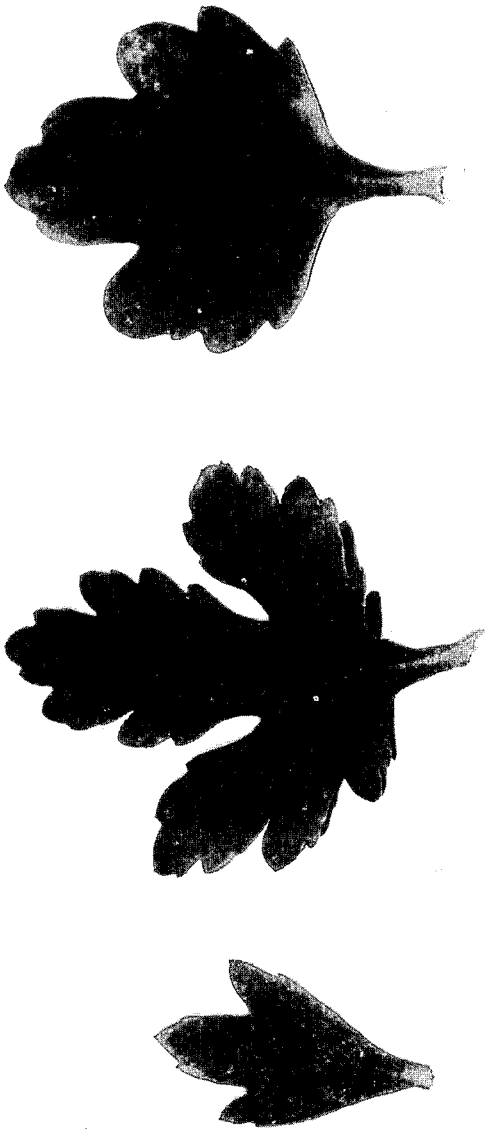

Plant Pat. 3,898
Patented June 1, 1976

3,898

CHRYSANTHEMUM PLANT

Grace H. Mack, New Canaan, Conn., and Walter H. Jessel, Jr., Doylestown, and William Erwin Duffett, Akron, Ohio, assignors to Grace H. Mack, New Canaan, Conn.

Filed Apr. 25, 1975, Ser. No. 571,477
Int. Cl. A01h *5/00*
U.S. Cl. Plt.—75 1 Claim

The present invention comprises a new and distinct cultivar of *Chrysanthemum morifolium,* Ramat., hereinafter referred to by the cultivar name Freedom (#70022M10).

Freedom was originated from a cross made by Grace H. Mack in a controlled breeding program in New Canaan, Conn. in the year 1969. The male, or pollen parent, was 959 (#21700E14; unnamed seedling), a yellow decorative of parentage unknown to the present inventors. The female, or seed parent, was Darlingmum (Golden Seedling, #21700E13; unpatented; commercially available), a yellow decorative of parentage unknown to the present inventors.

Freedom was discovered and selected as a flowering seedling within the progeny of the stated cross by Grace H. Mack and Walter H. Jessel, Jr. on Oct. 19, 1970 in an outdoor field environment in Barberton, Ohio.

Freedom is a product of a planned breeding program which had the objective of creating durable yellow decoratives for outdoor natural season field culture with early response, compact and spreading growth habit, and prolific flowering traits.

The first act of asexual reproduction of Freedom was accomplished when vegetative cuttings were taken from the initial selection in February 1971 in a controlled environment in Barberton, Ohio by a technician working under formulations established and supervised by William E. Duffett and Walter H. Jessel, Jr. Horticultural examination of selected units initiated Aug. 24, 1971 has demonstrated that the combination of characteristics as herein disclosed for Freedom are firmly fixed and are retained through successive generations of asexual reproduction.

Freedom has not been observed under all possible environmental conditions. The phenotype may vary significantly with variations in environment such as temperature, light intensity, and daylength. The following observations, measurements, and comparisons describe plants grown in a field in Barberton, Ohio under outdoor environmental conditions which are generally described in Local Climatological Data, Annual Summary With Comparative Data, Akron, Ohio. U.S. Department of Commerce, National Oceanic and Atmospheric Administration, Environmental Data Service. Washington, D.C.

1972, 1973, 1974 and Tables of Sunrise, Sunset, and Twilight. Supplement to the American Emphemeris, 1946. U.S. Naval Observatory, Washington, D.C., pg. 103.

The following traits have been repeatedly observed and are determined to be basic characteristics of Freedom which in combination distinguish this chrysanthemum as a new and distinct cultivar:

(1) Dark yellow inflorescence color.
(2) Flat inflorescence form.
(3) Decorative inflorescence type.
(4) Medium plant height.
(5) Semi-spreading plant growth habit.
(6) Average natural season flower date of October 1.
(7) Average controlled flowering response period of 7 weeks.
(8) Diameter of face of inflorescence up to 2 inches at maturity.

The accompanying photographic drawings show typical inflorescence and foliage characteristics of Freedom with colors being as nearly true as possible with illustrations of this type. Sheet 1 is a color photograph of Freedom. Sheet 2 is a black and white photograph showing three different views of the influorescence of Freedom. Sheet 3 is a black and white photograph showing the foliage of Freedom at three stages of growth.

Of the many commercial cultivars known to the present inventors, the most similar existing cultivars in comparison to Freedom are Goldtone (U.S. Plant Pat. #3,276), Jackpot (U.S. Plant Pat. #3,277) and Pixie Cushion (U.S. Plant Pat. #3,454). Reference is made to Chart A which is attached at the end of the present specification which compares certain characteristics of the above mentioned cultivars with the same characteristics of Freedom. General comparisons are as follows:

(1) In comparison to Goldton, Freedom has an earlier natural season flower date and smaller diameter across face of inflorescence. The inflorescence type and form, plant height, growth habit, inflorescence color, and controlled flowering response period of Freedom are similar to those of Goldtone.

(2) In comparison to Jackpot, Freedom has smaller diameter across face of inflorescence, taller height, and more intense inflorescence color. The natural season flower date, inflorescence form and type, growth habit, and controlled flowering response period of Freedom are similar to those of Jackpot.

(3) In comparison to Pixie Cushion, Freedom has later natural season flower date, taller height, more spreading growth habit, more intense inflorescence color, and longer controlled flowering response period. The inflorescence form and type of Freedom are similar to those of Pixie Cushion.

In the following description, color references are made to The Munsell Limit Color Cascade, 1972 edition. The color values were determined between 7:30 a.m. and 8:00 a.m. on Oct. 15, 1974 under 25 foot candle light intensity at Barberton, Ohio.

Botanical classification: *Chrysanthemum morifolium*, Ramat., cv Freedom.

I. INFLORESCENCE

A. Capitulum:
*Form.*—Flat.
*Type.*—Decorative.
*Diameter across face.*—1.5 to 2 inches.

II. PLANT

A. General appearance: Medium height; compact; semi-spreading.
B. Duration and texture: Perennial; herbaceous.
C. Stem color: 24–15.
D. Foliage:
*Color (abaxial).*—21–24.
*Color (adaxial).*—21–12 with more grey.
*Shape.*—Spatulate; deeply lobed.
*Texture.*—Glabrous.
*Arrangement.*—Alternate.
*Veination.*—Prominent.
*Margin.*—Coarsely serrated.

CHART A—COMPARISON OF FREEDOM WITH GOLDTONE, JACKPOT AND PIXIE CUSHION

| Cultivar | Natural season flower date | Diameter across face of inflorescence, inches | Inflorescence form and type | Plant height | Growth habit | Inflorescence color | Controlled flowering response period |
|---|---|---|---|---|---|---|---|
| Freedom | Oct. 1 | 1½–2 | Flat, decorative | Medium | Compact, semispreading | Dark yellow | 7 weeks. |
| Goldtone | Oct. 3 | 2–2½ | do | do | do | do | Do. |
| Jackpot | Oct. 1 | 2–2¾ | do | Short | do | Yellow | Do. |
| Pixie Cushion | Sept. 20 | 1½–1¾ | do | do | Compact, semiupright | do | 6 weeks |

B. Corolla of ray florets:
*Texture (adaxial).*—Glabrous.
*Appearance and form.*—Ligulate.
*Arrangement.*—Whorled on receptacle.
*Persistence.*—Resists shatter.
*Color (abaxial).*—26–5.
*Color (adaxial).*—26–5.
C. Reproductive organs:
*Androecium.*—Present disc florets only; syngenesious stamen; scant pollen.
*Gynoecium.*—Present both ray and disc florets; inferior, bicarpellate ovary; single style; 2-lobed stigma.

We claim:

1. A new and distinct cultivar of chrysanthemum plant characterized particularly as to uniqueness by the combined characteristics of dark yellow inflorescene color, flat inflorescence form, decorative inflorescence type, medium plant height, semi-spreading plant growth habit, average natural season flower date of October 1, average controlled flowering response period of seven weeks, and diameter of face of inflorescence up to 2 inches at maturity.

No references cited.

ROBERT E. BAGWILL, Primary Examiner